United States Patent
Krishna Rao et al.

(10) Patent No.: US 10,642,656 B2
(45) Date of Patent: May 5, 2020

(54) SYSTEM AND METHOD FOR EFFICIENTLY AND SECURELY MANAGING A NETWORK USING FOG COMPUTING

(71) Applicant: Cognizant Technology Solutions India Pvt. Ltd., Chennai (IN)

(72) Inventors: Geelapaturu Subrahmanya Venkata Radha Krishna Rao, Chennai (IN); Natarajan Venkatachalam, Coimbatore (IN); Anuj Kulshreshtha, Bhopal (IN)

(73) Assignee: COGNIZANT TECHNOLOGY SOLUTIONS INDIA PVT. LTD., Chennai (IN)

( * ) Notice: Subject to any disclaimer, the term of this patent is extended or adjusted under 35 U.S.C. 154(b) by 57 days.

(21) Appl. No.: 16/008,502

(22) Filed: Jun. 14, 2018

(65) Prior Publication Data

US 2019/0317818 A1 Oct. 17, 2019

(30) Foreign Application Priority Data

Apr. 17, 2018 (IN) .............................. 201841014541

(51) Int. Cl.
  *G06F 9/50* (2006.01)
  *H04L 29/08* (2006.01)
  *G16H 40/40* (2018.01)

(52) U.S. Cl.
  CPC .......... *G06F 9/5027* (2013.01); *G16H 40/40* (2018.01); *H04L 67/10* (2013.01); *H04L 67/12* (2013.01); *H04L 67/32* (2013.01)

(58) Field of Classification Search
  None
  See application file for complete search history.

(56) References Cited

U.S. PATENT DOCUMENTS 10,291,480 B2 * 5/2019 Pignataro .............. H04L 41/142
2015/0256475 A1 * 9/2015 Suman .................... H04L 47/70
709/226

(Continued)

OTHER PUBLICATIONS

Andrew Meola, "The roles of cloud computing and fog computing in the Internet of Things revolution", Dec. 20, 2016, Internet, URL: http://www.businessinsider.com/internet-of-things-cloud-computing-2016-10?IR=T.

(Continued)

*Primary Examiner* — Backhean Tiv
(74) *Attorney, Agent, or Firm* — Cantor Colburn LLP

(57) ABSTRACT

A system and computer-implemented method for managing a smart devices network using fog computing is provided. The system comprises an application manager configured to receive service requests from devices in a smart devices network and collect data related to fog computing nodes and intermediate computing nodes and a resource utilization predictor configured to predict availability of the fog computing nodes and the intermediate computing nodes. Furthermore, the system comprises a resource manager configured to dynamically allocate at least one of: a specific fog computing node and a specific intermediate computing node, schedule triggering of fog applications based on the predicted availability, trigger, at the specific fog computing node and the specific intermediate computing node, the fog applications for executing the received service requests corresponding to the devices and perform actions corresponding to the executed one or more service requests.

11 Claims, 3 Drawing Sheets

(56) References Cited

U.S. PATENT DOCUMENTS

| | | | |
|---|---|---|---|
| 2016/0321115 A1* | 11/2016 | Thorpe | H04L 47/823 |
| 2016/0359664 A1 | 12/2016 | Malegaonkar | |
| 2017/0048308 A1* | 2/2017 | Qaisar | H04L 67/1002 |
| 2017/0060574 A1 | 3/2017 | Malladi | |
| 2017/0228258 A1* | 8/2017 | Shifman | H04L 67/10 |
| 2017/0272342 A1* | 9/2017 | Zessin | H04L 41/12 |
| 2017/0337091 A1* | 11/2017 | Liu | G06F 9/5038 |
| 2017/0366472 A1* | 12/2017 | Byers | H04W 4/70 |
| 2018/0020062 A1* | 1/2018 | Li | H04W 4/70 |
| 2018/0219783 A1* | 8/2018 | Pfister | H04L 45/34 |
| 2018/0324636 A1* | 11/2018 | Laha | H04L 41/0686 |
| 2018/0331885 A1* | 11/2018 | Raymond | H04L 47/76 |
| 2019/0043201 A1* | 2/2019 | Strong | G06T 7/11 |
| 2019/0140933 A1* | 5/2019 | Guim Bernat | H04L 43/16 |
| 2019/0158606 A1* | 5/2019 | Guim Bernat | H04L 67/34 |
| 2019/0245806 A1* | 8/2019 | Hanes | H04L 47/808 |
| 2019/0258631 A1* | 8/2019 | Pal | G06F 16/2425 |

OTHER PUBLICATIONS

Ben Dickson, "How fog computing pushes IoT intelligence to the edge", TechCrunch, Aug. 2, 2016, Internet, URL: https://techcrunch.com/2016/08/02/how-fog-computing-pushes-iot-intelligence-to-the-edge/.

Janakiram MSV, "Is Fog Computing the Next Big Thing in Internet of Things?", Forbes, Apr. 18, 2016, Internet, URL: https://www.forbes.com/sites/janakirammsv/2016/04/18/is-fog-computing-the-next-big-thing-in-internet-of-things/#87043d7608df.

* cited by examiner

SYSTEM AND METHOD FOR EFFICIENTLY AND SECURELY MANAGING A NETWORK USING FOG COMPUTING

CROSS REFERENCE TO RELATED APPLICATION

This application is related to and claims the benefit of Indian Patent Application Number 201841014541 filed on Apr. 17, 2018, the contents of which are herein incorporated by reference in their entirety.

FIELD OF THE INVENTION

The present invention relates generally to fog computing. More particularly, the present invention provides a system and method for efficiently and securely managing a network using fog computing.

BACKGROUND OF THE INVENTION

In the past, healthcare industry mainly relied on doctor's personal experience, domain knowledge, patient's health condition and diagnostic laboratory reports for decision making.

However, there has been a tremendous influx of technology in last few years in all areas including healthcare. Particularly, usage of Internet of Things (IoT) based medical devices and mobile devices has increased manifold in the healthcare industry which has completely changed the decision making process.

Conventionally, healthcare organizations adopted various medical technologies and allowed use of mobile devices to create, store and transfer healthcare data. However, with such rampant increase in use of technology, data security challenges have also increased. Securely collecting, transmitting and storing healthcare data is a major drawback of many existing technologies used by the healthcare industry. Further, relying on complex medical systems employed by the healthcare organizations contribute to increasing number of healthcare accidents as well. The current safety engineering techniques that are widely practiced by the healthcare industry are inadequate in preventing these healthcare accidents.

In light of the above-mentioned disadvantages, there is a need for a system and method for efficiently and securely managing a network, particularly healthcare network, using fog computing. Further, there is a need for a system and method that securely stores the healthcare data and provides secure applications for sending and processing healthcare data using fog computing techniques. Furthermore, there is a need for a system and method that protects critical infrastructure and improves user experience, eliminates unsecured and unmanaged use of IoT based personal devices and reduce healthcare expenses. In addition, there is a need for a low-cost system and method that is capable of analyzing healthcare data closer to the devices that produce and act on it.

SUMMARY OF THE INVENTION

A system, computer-implemented method and computer program product for managing a smart devices network using fog computing is provided. The system comprises an application manager configured to receive one or more service requests from one or more devices in a smart devices network and collect data related to one or more fog computing nodes and one or more intermediate computing nodes. The system further comprises a resource utilization predictor configured to predict availability of the one or more fog computing nodes and the one or more intermediate computing nodes based on the collected data and the one or more received service requests. Furthermore, the system comprises a resource manager configured to dynamically allocate at least one of: a specific fog computing node and a specific intermediate computing node and schedule triggering of one or more fog applications based on the predicted availability. The resource manager is further configured to trigger, at the specific fog computing node and the specific intermediate computing node, the one or more fog applications for executing each of the one or more received service requests corresponding to the one or more devices. Also, the resource manager is configured to perform, at the specific fog computing node and the specific intermediate computing node, one or more actions corresponding to the executed one or more service requests.

In an embodiment of the present invention, the one or more devices in the smart devices network comprise one or more mobile devices, one or more hospital room devices, one or more medical devices and any other devices used in healthcare industry. In an embodiment of the present invention, the collected data related to the one or more fog computing nodes and the one or more intermediate computing nodes comprise availability, scheduled service requests, current service requests and time required for execution of service requests.

In an embodiment of the present invention, the resource utilization predictor predicts availability of the one or more fog computing nodes and the one or more intermediate computing nodes using a convolution neural network. In an embodiment of the present invention, triggering the one or more fog applications comprises execution of the one or more received service requests which further comprises execution of a series of jobs at the specific fog computing node and the specific intermediate computing node.

The computer-implemented method for managing a smart devices network using fog computing, via program instructions stored in a memory and executed by a processor, comprises receiving one or more service requests from one or more devices in a smart devices network. The computer-implemented method further comprises collecting data related to one or more fog computing nodes and one or more intermediate computing nodes. Furthermore, the computer-implemented method comprises predicting availability of the one or more fog computing nodes and the one or more intermediate computing nodes based on the collected data and the one or more received service requests. The computer-implemented method also comprises dynamically allocating at least one of: a specific fog computing node and a specific intermediate computing node and scheduling triggering of one or more fog applications based on the predicted availability. In addition, the computer-implemented method comprises triggering, at the specific fog computing node and the specific intermediate computing node, the one or more fog applications for executing of each of the one or more received service requests corresponding to the one or more devices. The computer-implemented method further comprises performing, at the specific fog computing node and the specific intermediate computing node, one or more actions corresponding to the executed one or more service requests.

The computer program product for managing a smart devices network using fog computing comprises a non-transitory computer-readable medium having computer-readable program code stored thereon, the computer-readable program code comprising instructions that when executed by a processor, cause the processor to receive one or more service requests from one or more devices in a smart devices network. The processor further collects data related to one or more fog computing nodes and one or more intermediate computing nodes. Furthermore, the processor predicts availability of the one or more fog computing nodes and the one or more intermediate computing nodes based on the collected data and the one or more received service requests. The processor also dynamically allocates at least one of: a specific fog computing node and a specific intermediate computing node and schedules triggering of one or more fog applications based on the predicted availability. In addition, the processor triggers, at the specific fog computing node and the specific intermediate computing node, the one or more fog applications for executing of each of the one or more received service requests corresponding to the one or more devices. The processor further performs, at the specific fog computing node and the specific intermediate computing node, one or more actions corresponding to the executed one or more service requests.

BRIEF DESCRIPTION OF THE ACCOMPANYING DRAWINGS

The present invention is described by way of embodiments illustrated in the accompanying drawings wherein.

DETAILED DESCRIPTION OF THE INVENTION

A system and method for efficiently and securely managing a network using fog computing is described herein. The invention provides a system and method that securely stores healthcare data and provides secure applications for sending and processing data using fog computing techniques. Furthermore, the invention provides a system and method that improves user experience, eliminates unsecured and unmanaged use of personal devices and reduces healthcare expenses. The invention also provides a low-cost system and method that is capable of analyzing healthcare data closer to the devices that produce and act on it.

The following disclosure is provided in order to enable a person having ordinary skill in the art to practice the invention. Exemplary embodiments are provided only for illustrative purposes and various modifications will be readily apparent to persons skilled in the art. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

The present invention would now be discussed in context of embodiments as illustrated in the accompanying drawings.

Figure 1:
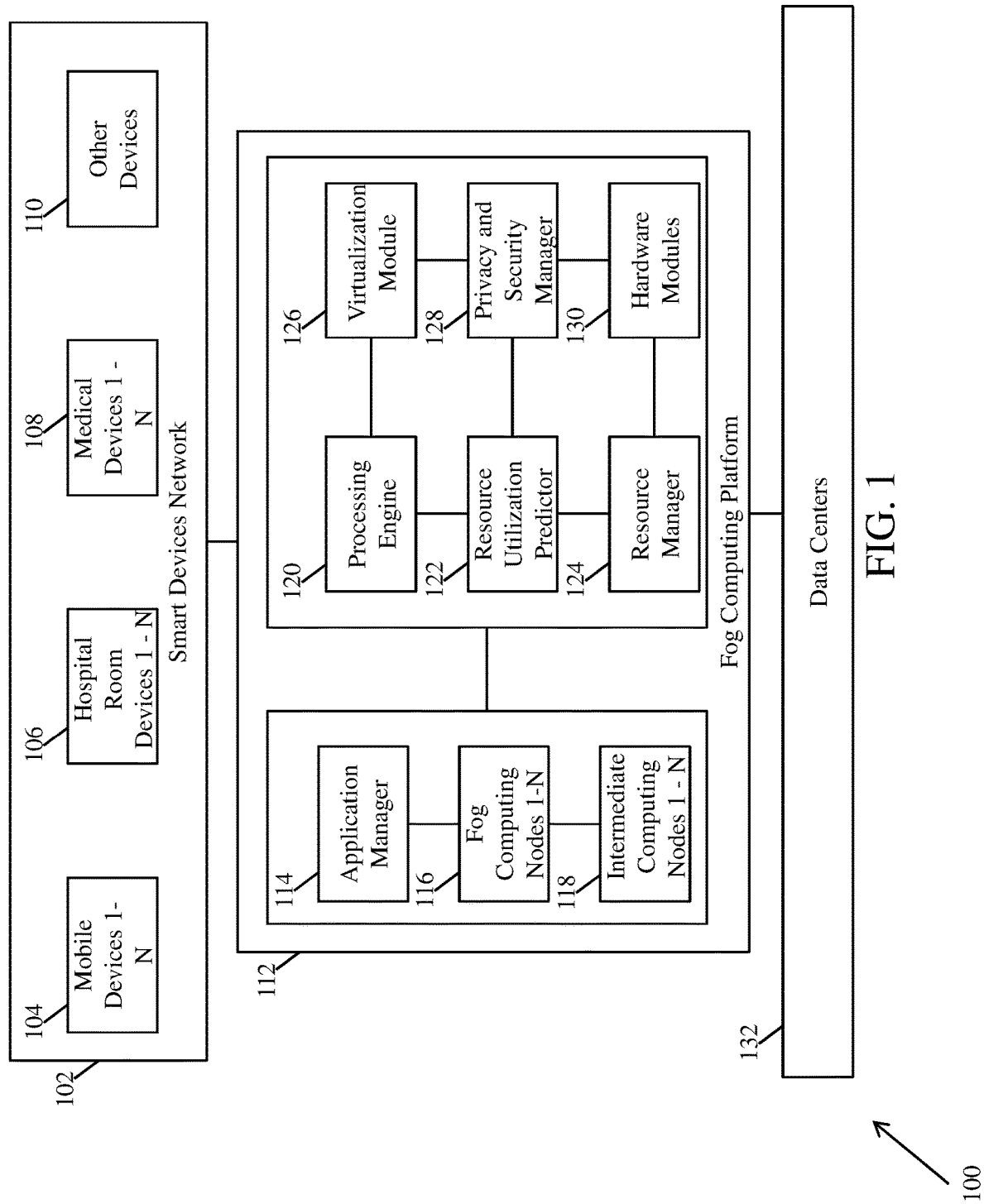
FIG. 1 is a block diagram illustrating a system for efficiently and securely managing a network using fog computing, in accordance with an embodiment of the present invention.

FIG. 1 is a block diagram illustrating a system 100 for efficiently and securely managing a network using fog computing, in accordance with an embodiment of the present invention. The system 100 comprises a smart devices network 102, a fog computing platform 112 and data centers 132.

The smart devices network 102 is an ecosystem of connected physical devices (also referred to as Internet of Things (IoT) devices) that interact through internet. In an exemplary embodiment of the present invention, the smart devices network 102 comprises various devices such as, but not limited to, one or more mobile devices 104, one or more hospital room devices 106, one or more medical devices 108 and any other devices 110 used in healthcare industry. The system 100 is not limited to healthcare industry and may be deployed in any other industry/sector/environment such as, but not limited to, smart grid deployments, vehicle-to-vehicle communication systems, manufacturing industry, smart cities and any other vertical.

The fog computing platform 112 comprises an application manager 114, one or more fog computing nodes 116, one or more intermediate computing nodes 118, a processing engine 120, a resource utilization predictor 122, a resource manager 124, a virtualization module 126, a privacy and security manager 128 and one or more hardware modules 130.

The application manager 114 is configured to collect data related to utilization of the one or more fog computing nodes 116, the one or more intermediate computing nodes 118 and the data centers 132. Further, the data related to utilization of the one or more fog computing devices 116, the one or more intermediate computing nodes 118 and the data centers 132 includes, but not limited to, availability, scheduled service requests, current service requests and time required for execution of service requests. The one or more fog computing nodes 116 comprise low and high power computing nodes that are also referred to as multiservice edge devices. Each fog computing node 116 controls a local group of IoT devices in a neighborhood or a small community and perform data analysis for service requests originating from those IoT devices in a timely manner using one or more fog applications. The one or more fog applications reside within the application manager 114. In an embodiment of the present invention, each fog computing node 116 is able to process, analyze and determine optimal health patterns using the data from the corresponding IoT devices (which forms service requests) and takes appropriate action such as, but not limited to, prompting the IoT devices to send signal to actuators within the system 100 to transmit data or notify medical staff and family members via the one or more mobile devices 104. The one or more intermediate computing nodes 118, also referred to as edge servers, are configured to control a group of fog computing nodes 116. The one or more intermediate computing nodes 118 are capable of associating spatial and temporal data to identify emergency situations (that form service requests) and responding whenever emergency situations are identified. The results of the processing and analysis performed by the one or more fog computing nodes 116 and the one or more intermediate computing nodes 118 are transferred to the data centers 132. The data centers 132 are existing cloud based resources that are centrally deployed for monitoring and controlling various operations of the network such as, but not limited to, the healthcare network. The data centers 132 are capable of performing complex processing, wide behavior analysis, advanced analytics, complex machine learning tasks and storage.

During operation, the application manager 114 collects the data related to utilization of the one or more fog computing nodes 116, the one or more intermediate computing nodes 118 and the data centers 132 at pre-configured intervals such as, but not limited to, every minute, once every ten minutes or every hour and sorts the collected data into buffers. The application manager 114 also provides services for collecting, aggregating and storing data, network information, application details, device details and business group details from the various IoT devices residing in the smart devices network 102. The application manager 114 further collects and stores, in the buffers, user fed information such as, but not limited to, application customization information, resource constraints and priority level of application from the various IoT devices residing in the smart devices network 102. Once the collected data is stored in the buffers, control is transferred to the processing engine 120.

The processing engine 120 is configured to receive the data stored in the buffers and check the received data for data normality. In an embodiment of the present invention, the data is passed through a filter to perform data smoothing and de-noising prior to checking for normality. In an exemplary embodiment of the present invention, once the received data is passed through the filter, the normality of the data is estimated using Pearson's Chi-squared test with 5% significance level. If the data passes the normality test then the control is transferred to the resource utilization predictor 122. If the data does not pass the normality test, then the data is passed through the filter again and various filtering techniques and transformations are applied for data smoothing and de-noising.

Once the data passes the normality test, the resource utilization predictor 122 analyzes volume of service requests, tuning parameters and hardware availability using the normalized data. The resource utilization predictor 122 then predicts availability of the one or more fog nodes 116 and the one or more intermediate computing nodes 118 for one or more service requests originating from the one or more IoT devices residing in the smart devices network 102. The one or more service requests include, but not limited to, triggers that facilitate performing one or more actions such as, but not limited to, fetching additional data, processing, computing and sending alerts. In an exemplary embodiment of the present invention, in case the system 100 is deployed in a healthcare environment, a service request is in the form of a trigger when blood pressure monitoring device determines that the blood pressure is below or above a pre-set threshold value. In an exemplary embodiment of the present invention, in case the system 100 is deployed for managing traffic, a service request is in the form of a trigger/request for turning a smart traffic light green in case the IoT devices or access points determine that an ambulance is present and waiting for the traffic light to change.

The resource utilization predictor 122 is an intelligence driven system which is advantageous during peak workload traffic and deadlocks. During operation, the resource utilization predictor 122 analyzes the type of service request, volume of data corresponding to the service request and business related information corresponding to the service request. The resource utilization predictor 122 also analyzes the usage of the one or more fog computing nodes 116 and the one or more intermediate computing nodes 118 and dynamically adjusts the operating voltage and reduces power utilization based on the frequency of fog clusters and their hardware components. The resource utilization predictor 122 then predicts availability and assigns the one or more fog nodes 116 and the one or more intermediate computing nodes 118 for the one or more service requests using a convolution neural network algorithm. Also, the resource utilization predictor 122 has user-defined parameter settings for the one or more fog applications to prioritize highly critical and emergency situations thereby making the system 100 adaptable to fluctuations and providing reliable and efficient services. The resource utilization predictor 122 determines the one or more fog applications required for the one or more service requests based on the predicted availability of the one or more fog computing nodes 116 and the one or more intermediate computing nodes 118.

Once the resource utilization predictor 122 predicts availability of the one or more fog computing nodes 116 and the one or more intermediate computing nodes 118, the one or more service requests received from the one or more IoT devices are allocated dynamically to a specific fog computing node 116 or a specific intermediate computing node 118 based on the predicted availability. Further, the one or more fog applications are also scheduled for triggering. Furthermore, the IoT device corresponding to the service request is connected with the specific fog node 116 or the specific intermediate computing node 118. The resource utilization predictor 122 then provides information related to availability of the computational resources to the processing engine 120 which then reconfigures the computational resources such as, but not limited to, the one or more fog computing nodes 116, the one or more intermediate computing nodes 118 and the data centers 132, network bandwidth and job priorities thereby increasing the performance of the computational resources and enabling the computational resources to adapt to different work load traffic patterns and critical situations.

The resource manager 124 is also configured to schedule triggering of the one or more fog applications that are pushed to the one or more fog computing nodes 116 and the one or more intermediate computing nodes 118. The resource manager 124 comprise an application placement module and a resource scheduler that manages the available resources and minimize resource wastage. Further, the resource manager 124 applies separate policies to facilitate resource customization. The application placement module facilitates in pushing the one or more fog applications across the fog devices for execution of the one or more service requests.

The resource manager 124 enables triggering the one or more fog applications for execution of each of the one or more service requests corresponding to the one or more devices. Further, execution of the one or more received service requests include, but not limited to, execution of a series of jobs through a software program at the assigned and allocated fog computing node 116 and/or the intermediate computing node 118 within a pre-defined time. The resource manager 124 executes the one or more service requests at the fog resources based on the input from the resource utilization predictor 122. On execution of each of the one or more service requests, one or more actions are performed by the corresponding fog computing node 116 or the intermediate computing node 118. Further, information related to execution is then forwarded to the data centers 132.

In an embodiment of the present invention, fog applications include, but not limited to, intelligent traffic lights application. The intelligent traffic lights application facilitates actions such as, but not limited to, enabling traffic signals to open the lane by observing and sensing the flash light from an ambulance, identifying presence of pedestrians and bikers, measuring speed and distance of the vehicles and enhancing interactions between vehicle and access points using WiFi, 3G, road side units and smart traffic lights.

In an embodiment of the present invention, fog applications facilitate efficiently managing smart grids. The smart devices in the smart grid are facilitated to automatically switch to alternative energies like solar and winds based on the supply and demand for energy. Energy production and energy consumption data is collected from the energy management IoT devices such as, but not limited to, energy meters which is forwarded to various fog computing nodes 116. The one or more fog computing nodes 116 then collect the data and generate control commands for the actuators using the fog applications.

The virtualization module 126 is configured to provide a common interface for hiding the underlying hardware modules 130 from the application manager 114. Once the fog computing node 116 or the intermediate computing node 118 connected to a specific IoT device triggers a fog application for execution of the service request from the specific IoT device, the virtualization module 126 creates a virtual environment for the fog application thereby ensuring that each fog application has its own virtual instantiation running in the application manager 114. Also, prior to creating one or more virtual environments, the virtualization module 126, based on the information related to the availability of the computational resources, reformats previous service requests from the fog clusters to remove hardware and network dependency parameters thereby reducing operational burden on the application manager 114.

The privacy and security manager 128 is configured to secure the data which is transmitted within the system 100. The privacy and security manager 128 employs various mechanisms for securing the data and the system 100. The mechanisms employed by the privacy and security manager 128 include, but not limited to, wireless security protocols, data encryption and key management, secure communication protocols, firewalls, event and behavior monitoring and virtual machine and hypervisor security. In an embodiment of the present invention, for encryption Transport Layer Security (TLS) is used to encrypt data during transmission and validate endpoints to prevent Man-In-The-Middle (MITM) attacks. In an embodiment of the present invention, the privacy and security manager 128 limits the access to stored data, for example, write only APIs are employed to store network credentials and encrypting sensitive data on the IoT devices. In an embodiment of the present invention, for securing the data during communication, the security and privacy manager 128 facilitates use of TLS encryption on the IoT devices and communication with all the applications over HyperText Transfer Protocol (HTTP) using TLS protocol. Further, the privacy and security manager 128 uses existing cryptographic capabilities to generate public and private keys, embeds the public key and ensures that the private key is stored in the Advanced Encryption Standard (AES) encrypted part of the data. Encrypting the key facilitates protecting the key from being extracted by decrypted message and makes it difficult to impersonate the data.

The privacy and security manager 128 facilitates securing data at file level which can be extracted, processed and fed into different IoT devices without relying on additional functionality of third-party services. Further, the privacy and security manager 128 uses attribute based encryption method to secure the confidential data and define data security policies for each device and the users simultaneously.

The hardware modules 130 comprise power manager, data storage controller and other network resources. Further, the data storage controller and storage units are used to manage database and backup services in the cloud/datacenters 132. The network resources facilitate managing network connectivity between the one or more fog computing nodes 116 and the IoT devices residing in the smart device network 102 and between the one or more intermediate computing nodes 118 and the data centers 132.

The system 100 is an intelligent prediction system that offers a flexible platform on which organizations/enterprises/industries can deploy their own application components via the application manager 114. Further, the system 100 facilitates the organizations/enterprises/industries to create personalized computing environment and manage services tailored to the needs of individual users of the IoT devices. Personalization include, but not limited to, development of customized technology service plans for individuals' and groups with special needs. The system 100 also promotes greater capacity for self-management and self-organization of the IoT devices by creating a well-structured and matured fog computing model using powerful machine learning methods such as, but not limited to, CNN algorithms.

The system 100 facilitates in designing flexible systems and reducing use of remote data centers and cloud based systems thereby controlling costs and reducing latency. Further, the system 100 facilitates securing data at the file level which can be extracted, processed and fed into different IoT devices without relying on additional functionality of third-party services. Furthermore, the system 100 employs attribute based encryption methods to secure confidential data and define data security policies for each IoT device and their users simultaneously.

In an embodiment of the present invention, the system 100 is used for securing and managing IoT devices in a cyber physical system. The fog computing platform 112 enables building embedded systems in which software programs and the IoT devices are associated. In an embodiment of the present invention, the fog computing platform 112 works in conjunction with Software Defined Networks (SDNs) to resolve issues such as, but not limited to, vehicle network irregular connectivity, collisions and high packet loss rate.

In an embodiment of the present invention the system 100 is implemented to manage autonomous automobile systems. The fog computing platform 112 provides various features like automatic steering, self-parking and enabling varies operations of the vehicles. Further, the system 100 facilitates real-time secure interaction. Furthermore, vehicles, access points and traffic lights are able to efficiently interact thereby allowing safe and secure real-time access.

The system 100 provides fog computing based personalized computing environment for managing services tailored to the needs of individual organizations and specific industries. Further, the system 100 provides options for development and implementation of individualized technology service plans. Furthermore, the system 100 promotes self-management and self-organization of IoT devices by establishing well-structured and matured fog computing model.

Figure 2:
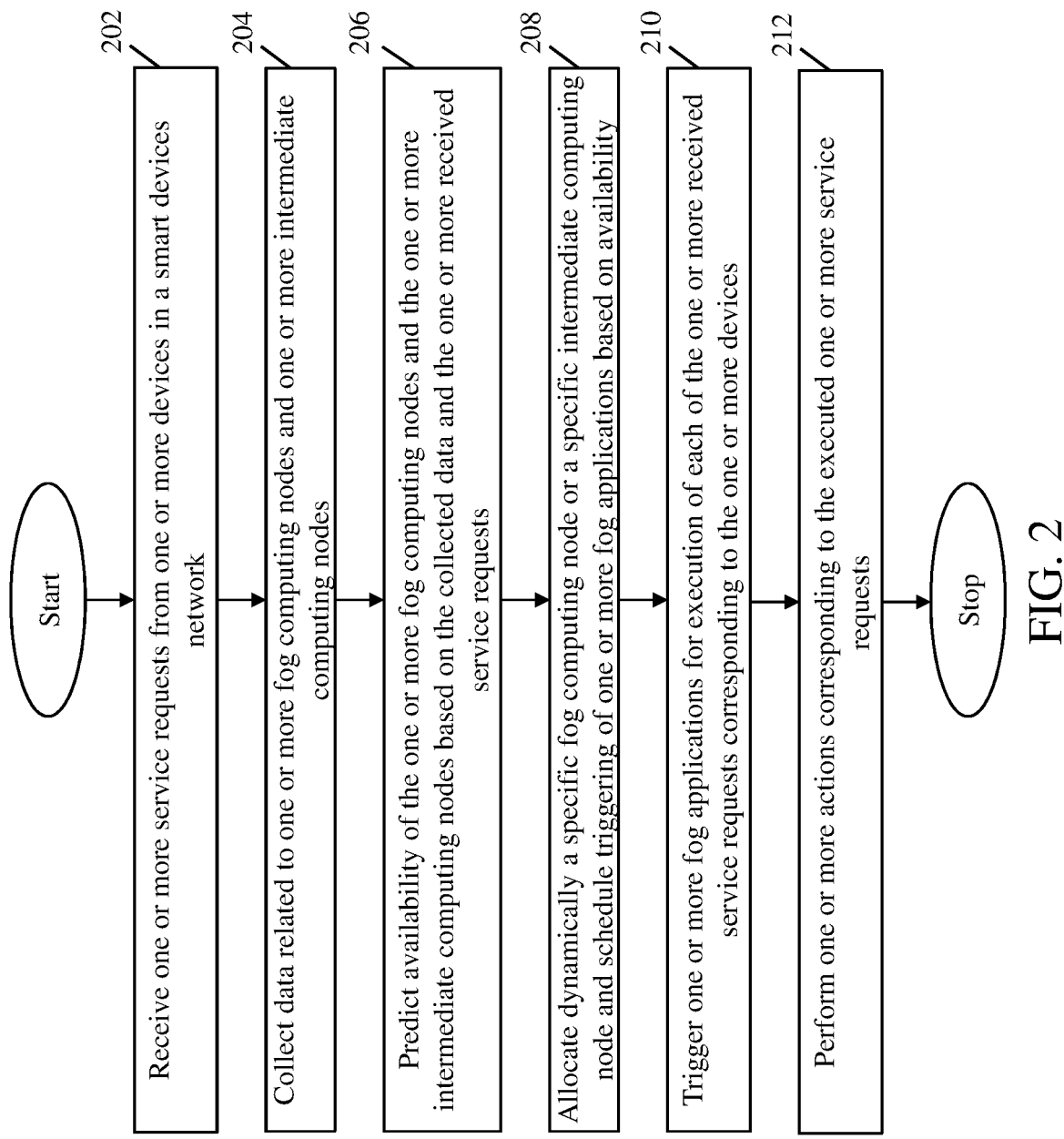
FIG. 2 is a flowchart illustrating a method for efficiently and securely managing a network using fog computing, in accordance with an embodiment of the present invention.

FIG. 2 is a flowchart illustrating a method for efficiently and securely managing a network using fog computing, in accordance with an embodiment of the present invention.

At step 202, one or more service requests are received from one or more devices in a smart devices network. The smart devices network is an ecosystem of connected physical devices (also referred to as Internet of Things (IoT) devices) that interact through internet. In an exemplary embodiment of the present invention, the smart devices network comprises various devices such as, but not limited to, one or more mobile devices, one or more hospital room devices, one or more medical devices and any other devices used in healthcare industry. Further, the smart devices network is not limited to the healthcare industry and may be deployed in any other industry/sector/environment such as, but not limited to, smart grid deployments, vehicle-to-vehicle communications systems, autonomous mobile monitoring systems, manufacturing industry, smart cities and any other vertical. The one or more service requests include, but not limited to, triggers that facilitate performing one or more actions such as, but not limited to, fetching additional data, processing, computing and sending alerts. The one or more devices in the smart device network are deployed and configured to collect data from one or more sources or generate the data which constitutes the one or more received service requests.

In an exemplary embodiment of the present invention, in case of a medical monitoring system, a service request is in the form of a trigger when blood pressure monitoring device (which is an IoT device) determines that the blood pressure is below or above a pre-set threshold value. In an exemplary embodiment of the present invention, in case of smart traffic lights system, a service request is in the form of a trigger/request from an access point (close to the smart traffic light or on the traffic light) for turning the smart traffic light green in case an ambulance is detected to be waiting for the traffic light signal to change.

At step 204, data related to one or more fog computing nodes, one or more intermediate computing nodes and data centers is collected at pre-configured intervals. The collected data is then sorted into buffers. Also, data such as, but not limited to, network information, application details, device details and business group details, from the IoT devices residing in the smart devices network, are also collected, aggregated and stored. Further, user fed information such as, but not limited to, application customization information, resource constraints and priority level of application, from the various IoT devices residing in the smart devices network, is also collected and stored in the buffers. The stored data is then normalized. In an embodiment of the present invention, the stored data is fetched and passed through a filter to perform data smoothing and de-noising prior to checking for normality. In an exemplary embodiment of the present invention, once the received data is passed through the filter, the normality of the data is estimated using Pearson's Chi-squared test with 5% significance level.

At step 206, availability of the one or more fog computing nodes and the one or more intermediate computing nodes is predicted based on the collected and normalized data and the one or more received service requests. The one or more fog computing nodes comprise low and high power computing nodes that are also referred to as multiservice edge devices. Each fog computing node controls a local group of IoT devices in a neighborhood or a small community and perform data analysis for service requests originating from those IoT devices in a timely manner using one or more fog applications. The one or more intermediate computing nodes, also referred to as edge servers, are configured to control a group of fog computing nodes. The one or more intermediate computing nodes are capable of associating spatial and temporal data to identify emergency situations and responding whenever emergency situations are identified. The results of the processing and analysis performed by the one or more fog computing nodes 116 and the one or more intermediate computing nodes 118 are transferred to the data centers 132. The data centers 132 are existing cloud based resources that are centrally deployed for monitoring and controlling various operations of the healthcare network. The data centers 132 are capable of performing complex processing, wide behavior analysis, advanced analytics, complex machine learning tasks and storage.

In an embodiment of the present invention, a convolution neural network algorithm is used which facilitates predicting availability and assigning/allocating the one or more fog nodes and the one or more intermediate computing nodes for each of the one or more service requests originating from the one or more IoT devices. Further, the one or more fog applications required for the one or more service requests are also determined based on the predicted availability of the one or more fog computing nodes and the one or more intermediate computing nodes and type of the service request.

At step 208, a specific fog computing node or a specific intermediate computing node is dynamically allocated for executing the one or more service requests. The one or more fog applications are also scheduled for triggering based on the predicted availability.

At step 210, the one or more fog applications are triggered for execution of each of the one or more service requests corresponding to the one or more devices. At step 212, one or more actions are performed corresponding to the executed one or more service requests. In an exemplary embodiment of the present invention, the one or more actions performed corresponding to an executed service request include, but not limited to, sending an alert on a doctor's mobile phone and on a nurse's mobile phone related to patient's blood pressure monitored by the blood pressure monitoring device connected to the smart device network of the hospital. In an exemplary embodiment of the present invention, the one or more actions performed corresponding to an executed service request from a smart traffic light include, changing the traffic light signal to green in case an ambulance is detected which is waiting for signal change.

Figure 3:
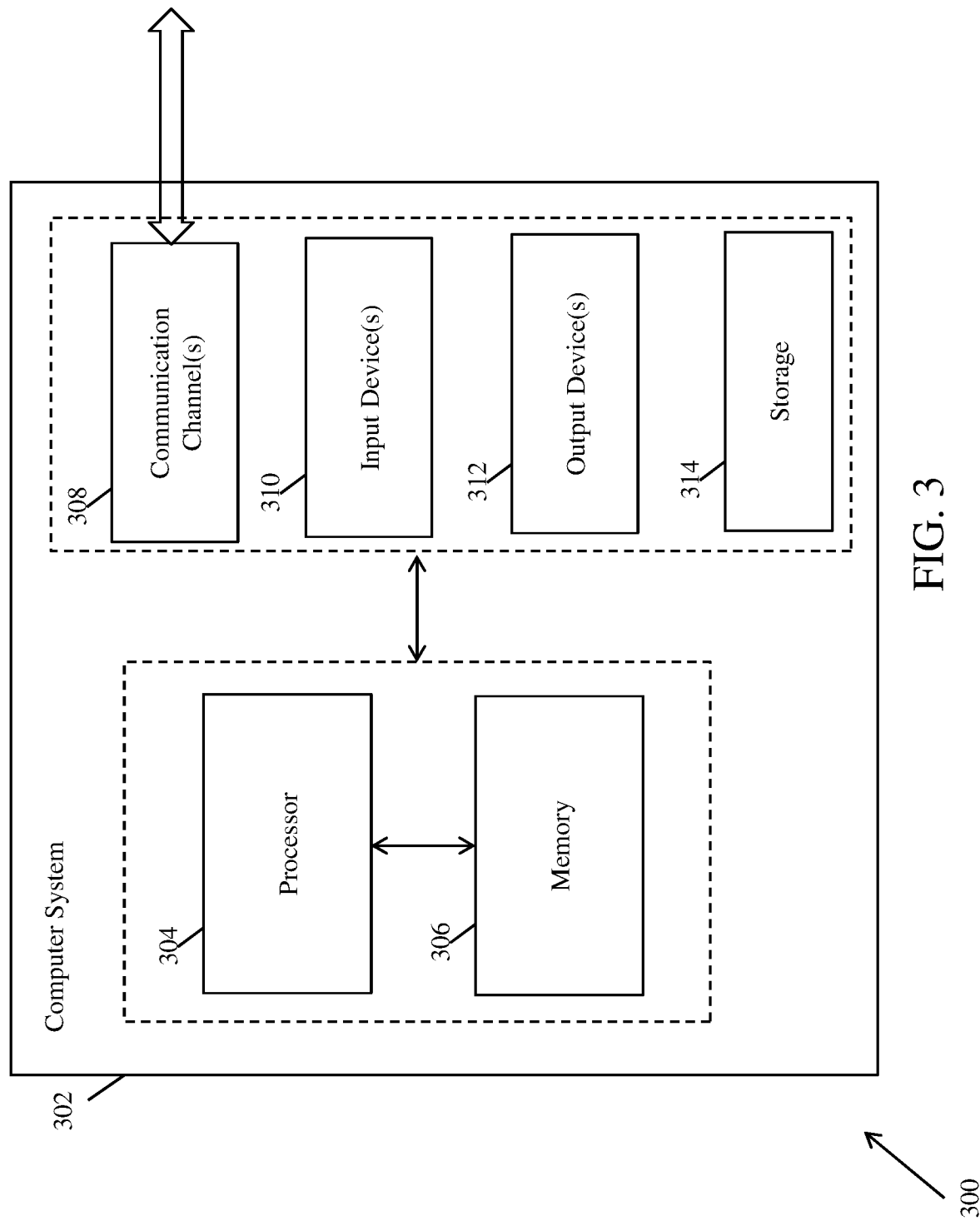
FIG. 3 illustrates an exemplary computer system for efficiently and securely managing a network using fog computing, in accordance with an embodiment of the present invention.

FIG. 3 illustrates an exemplary computer system for efficiently and securely managing a network using fog computing, in accordance with an embodiment of the present invention.

The computer system 302 comprises a processor 304 and a memory 306. The processor 304 executes program instructions and may be a real processor. The processor 304 may also be a virtual processor. The computer system 302 is not intended to suggest any limitation as to scope of use or functionality of described embodiments. For example, the computer system 302 may include, but not limited to, a general-purpose computer, a programmed microprocessor, a micro-controller, a peripheral integrated circuit element, and other devices or arrangements of devices that are capable of implementing the steps that constitute the method of the present invention. In an embodiment of the present invention, the memory 306 may store software for implementing various embodiments of the present invention. The computer system 302 may have additional components. For example, the computer system 302 includes one or more communication channels 308, one or more input devices 310, one or more output devices 312, and storage 314. An interconnection mechanism (not shown) such as a bus, controller, or network, interconnects the components of the computer system 302. In various embodiments of the present invention, operating system software (not shown) provides an operating environment for various softwares executing in the computer system 302, and manages different functionalities of the components of the computer system 302.

The communication channel(s) 308 allow communication over a communication medium to various other computing entities. The communication medium provides information such as program instructions, or other data in a communication media. The communication media includes, but not limited to, wired or wireless methodologies implemented with an electrical, optical, RF, infrared, acoustic, microwave, bluetooth or other transmission media.

The input device(s) 310 may include, but not limited to, a keyboard, mouse, pen, joystick, trackball, a voice device, a scanning device, or any another device that is capable of providing input to the computer system 302. In an embodiment of the present invention, the input device(s) 310 may be a sound card or similar device that accepts audio input in analog or digital form. The output device(s) 312 may include, but not limited to, a user interface on CRT or LCD, printer, speaker, CD/DVD writer, or any other device that provides output from the computer system 302.

The storage 314 may include, but not limited to, magnetic disks, magnetic tapes, CD-ROMs, CD-RWs, DVDs, flash drives or any other medium which can be used to store information and can be accessed by the computer system 302. In various embodiments of the present invention, the storage 314 contains program instructions for implementing the described embodiments.

The present invention may suitably be embodied as a computer program product for use with the computer system 302. The method described herein is typically implemented as a computer program product, comprising a set of program instructions which is executed by the computer system 302 or any other similar device. The set of program instructions may be a series of computer readable codes stored on a tangible medium, such as a computer readable storage medium (storage 314), for example, diskette, CD-ROM, ROM, flash drives or hard disk, or transmittable to the computer system 302, via a modem or other interface device, over either a tangible medium, including but not limited to optical or analogue communications channel(s) 308. The implementation of the invention as a computer program product may be in an intangible form using wireless techniques, including but not limited to microwave, infrared, bluetooth or other transmission techniques. These instructions can be preloaded into a system or recorded on a storage medium such as a CD-ROM, or made available for downloading over a network such as the internet or a mobile telephone network. The series of computer readable instructions may embody all or part of the functionality previously described herein.

The present invention may be implemented in numerous ways including as an apparatus, method, or a computer program product such as a computer readable storage medium or a computer network wherein programming instructions are communicated from a remote location.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims.

We claim:

1. A system for managing a smart devices network using fog computing, the system comprising:
    a memory storing program instructions;
    a processor configured to execute instructions stored in the memory and configured to:
        receive one or more service requests from one or more devices in a smart devices network;
        collect data related to one or more fog computing nodes and one or more intermediate computing nodes;
        predict availability of the one or more fog computing nodes and the one or more intermediate computing nodes based on the collected data and the one or more received service requests;
    dynamically allocate a specific fog computing node and a specific intermediate computing node and schedule triggering of one or more fog applications based on the predicted availability;
        trigger, at the specific fog computing node and the specific intermediate computing node, the one or more fog applications for executing each of the one or more received service requests corresponding to the one or more devices; and
        perform, at the specific fog computing node and the specific intermediate computing node, one or more actions corresponding to the executed one or more service requests.

2. The system of claim 1, wherein the one or more devices in the smart devices network comprise one or more mobile devices, one or more hospital room devices, one or more medical devices and any other devices used in healthcare industry.

3. The system of claim 1, wherein the collected data related to the one or more fog computing nodes and the one or more intermediate computing nodes comprise availability, scheduled service requests, current service requests and time required for execution of service requests.

4. The system of claim 1, wherein the resource utilization predictor predicts availability of the one or more fog computing nodes and the one or more intermediate computing nodes using a convolution neural network.

5. The system of claim 1, wherein triggering the one or more fog applications comprises execution of the one or more received service requests, which further comprises execution of a series of jobs at the specific fog computing node and the specific intermediate computing node.

6. A computer-implemented method for managing a smart devices network using fog computing, via program instructions stored in a memory and executed by a processor, the computer-implemented method comprising:
    receiving one or more service requests from one or more devices in a smart devices network;
    collecting data related to one or more fog computing nodes and one or more intermediate computing nodes;
    predicting availability of the one or more fog computing nodes and the one or more intermediate computing nodes based on the collected data and the one or more received service requests;
    dynamically allocating a specific fog computing node and a specific intermediate computing node and scheduling triggering of one or more fog applications based on the predicted availability;

triggering, at the specific fog computing node and the specific intermediate computing node, the one or more fog applications for executing of each of the one or more received service requests corresponding to the one or more devices; and performing, at the specific fog computing node and the specific intermediate computing node, one or more actions corresponding to the executed one or more service requests.

7. The computer-implemented method of claim 6, wherein the one or more devices in the smart devices network comprise one or more mobile devices, one or more hospital room devices, one or more medical devices and any other devices used in healthcare industry.

8. The computer-implemented method of claim 6, wherein the collected data related to the one or more fog computing nodes and the one or more intermediate computing nodes comprise availability, scheduled service requests, current service requests and time required for execution of service requests.

9. The computer-implemented method of claim 6, wherein the availability of the one or more fog computing nodes and the one or more intermediate computing nodes is predicted using a convolution neural network.

10. The computer-implemented method of claim 6, wherein triggering the one or more fog applications comprises execution of the one or more received service requests, which further comprises execution of a series of jobs at the specific fog computing node and the specific intermediate computing node.

11. A computer program product for managing a smart devices network using fog computing, the computer program product comprising:

a non-transitory computer-readable medium having computer-readable program code stored thereon, the computer-readable program code comprising instructions that when executed by a processor, cause the processor to:

receive one or more service requests from one or more devices in a smart devices network;

collect data related to one or more fog computing nodes and one or more intermediate computing nodes;

predict availability of the one or more fog computing nodes and the one or more intermediate computing nodes based on the collected data and the one or more received service requests;

dynamically allocate a specific fog computing node and a specific intermediate computing node and scheduling triggering of one or more fog applications based on the predicted availability;

trigger, at the specific fog computing node and the specific intermediate computing node, the one or more fog applications for executing of each of the one or more received service requests corresponding to the one or more devices; and perform, at the specific fog computing node and the specific intermediate computing node, one or more actions corresponding to the executed one or more service requests.

* * * * *